United States Patent [19]

Alvarez

[11] 4,198,403

[45] Apr. 15, 1980

[54] 17 BETA-THIOCARBOXYLIC ACID ESTERS OF 4-HALO-3-OXOANDROST-4-ENES

[75] Inventor: Francisco S. Alvarez, Sunnyvale, Calif.

[73] Assignee: Syntex (U.S.A.) Inc., Palo Alto, Calif.

[21] Appl. No.: 893,390

[22] Filed: Apr. 5, 1978

[51] Int. Cl.$^2$ .......................... C07J 7/00; A61K 31/58
[52] U.S. Cl. ..................................... 424/241; 424/243; 260/239.55 D; 260/397.1; 260/239.5
[58] Field of Search ...................... 260/397.1; 424/241, 424/243; /Steroids MS File

[56] References Cited

U.S. PATENT DOCUMENTS

| | | | |
|---|---|---|---|
| 3,989,686 | 11/1976 | Phillipps et al. | 260/397.1 |
| 4,093,721 | 6/1978 | Phillipps et al. | 424/243 |

FOREIGN PATENT DOCUMENTS 2707336  8/1977  Fed. Rep. of Germany ... 260/239.55 D

*Primary Examiner*—Elbert L. Roberts
*Attorney, Agent, or Firm*—Tom M. Moran; Gerard A. Blaufarb

[57] ABSTRACT

Certain 3-oxoandrost-4-ene and 3-oxoandrosta-1,4-diene 17 beta-thiocarboxylic acid esters substituted at the 4-position with a fluoro, chloro or bromo and optionally substituted at the six position with fluoro or chloro are useful as anti-inflammatory steroids. These compounds are optionally substituted at the 9 alpha position with fluoro, chloro or bromo; substituted at the 11 with a keto, a beta-hydroxy or a beta-chloro (the latter only when there is a 9 alpha-chloro); substituted at 16 alpha,-17 alpha-positions with isopropylidenedioxy; and substituted at 16 alpha (or 16 beta) with methyl or hydrogen when there is a 17 alpha-hydroxy (or an ester).

36 Claims, 5 Drawing Figures

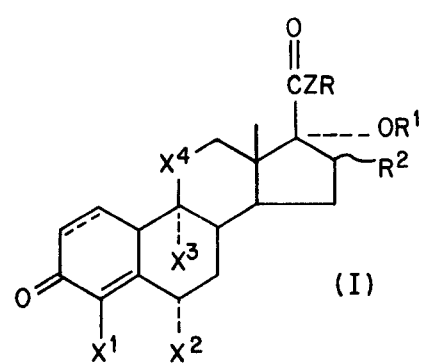
(I)
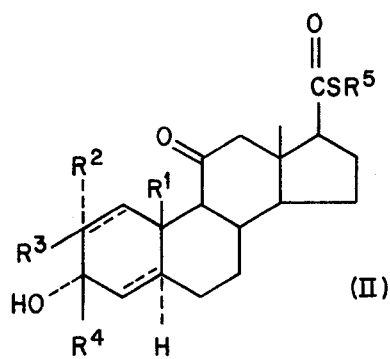
(II)

U.S. Patent Apr. 15, 1980 Sheet 2 of 6 4,198,403
REACTION SEQUENCE A
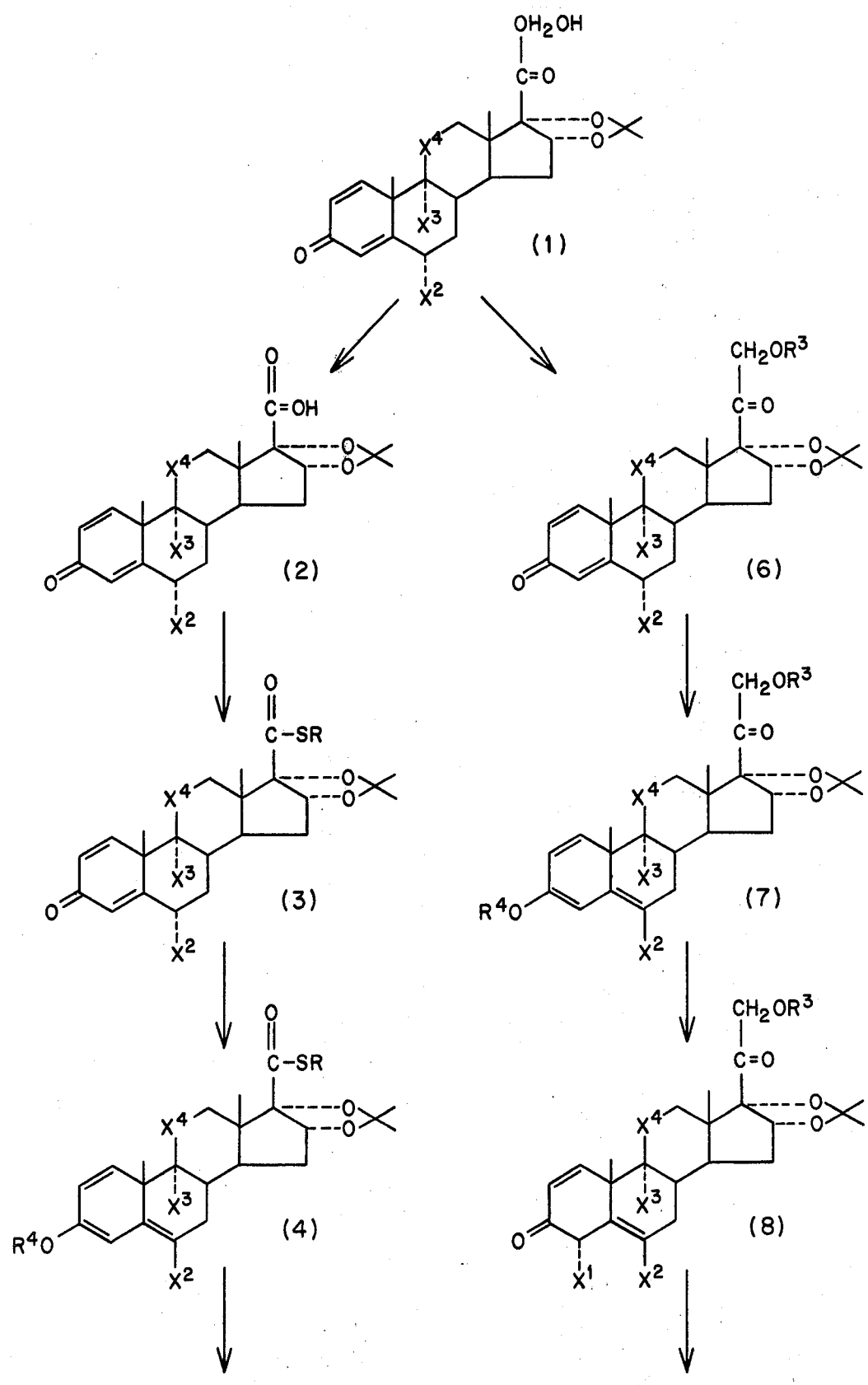

REACTION SEQUENCE A
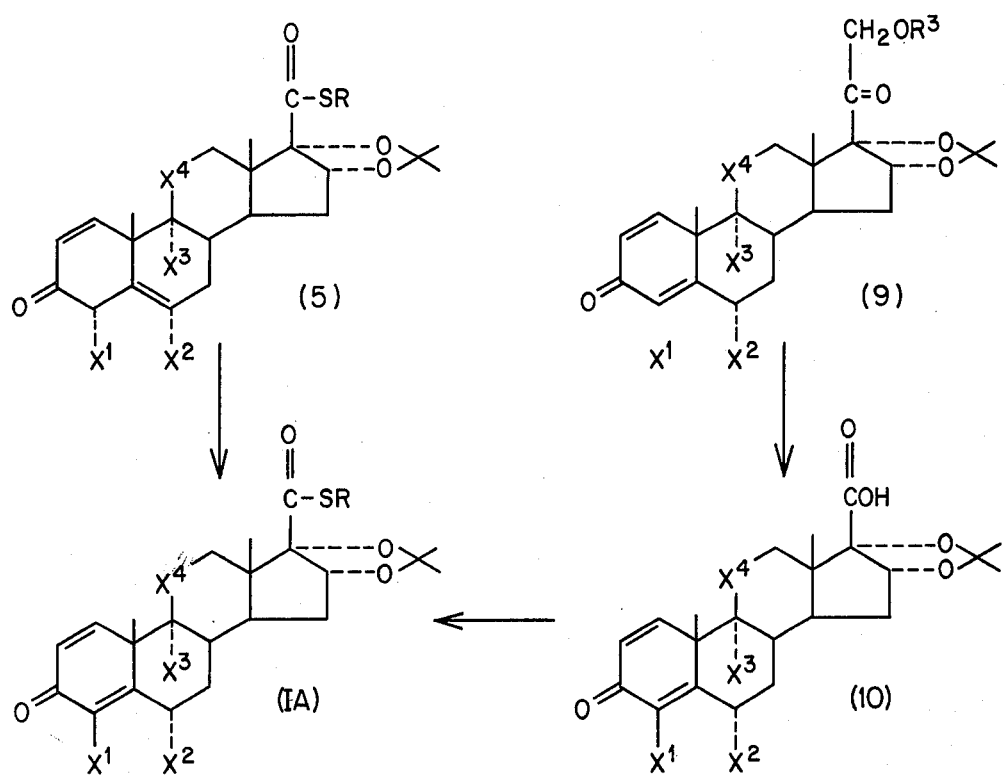

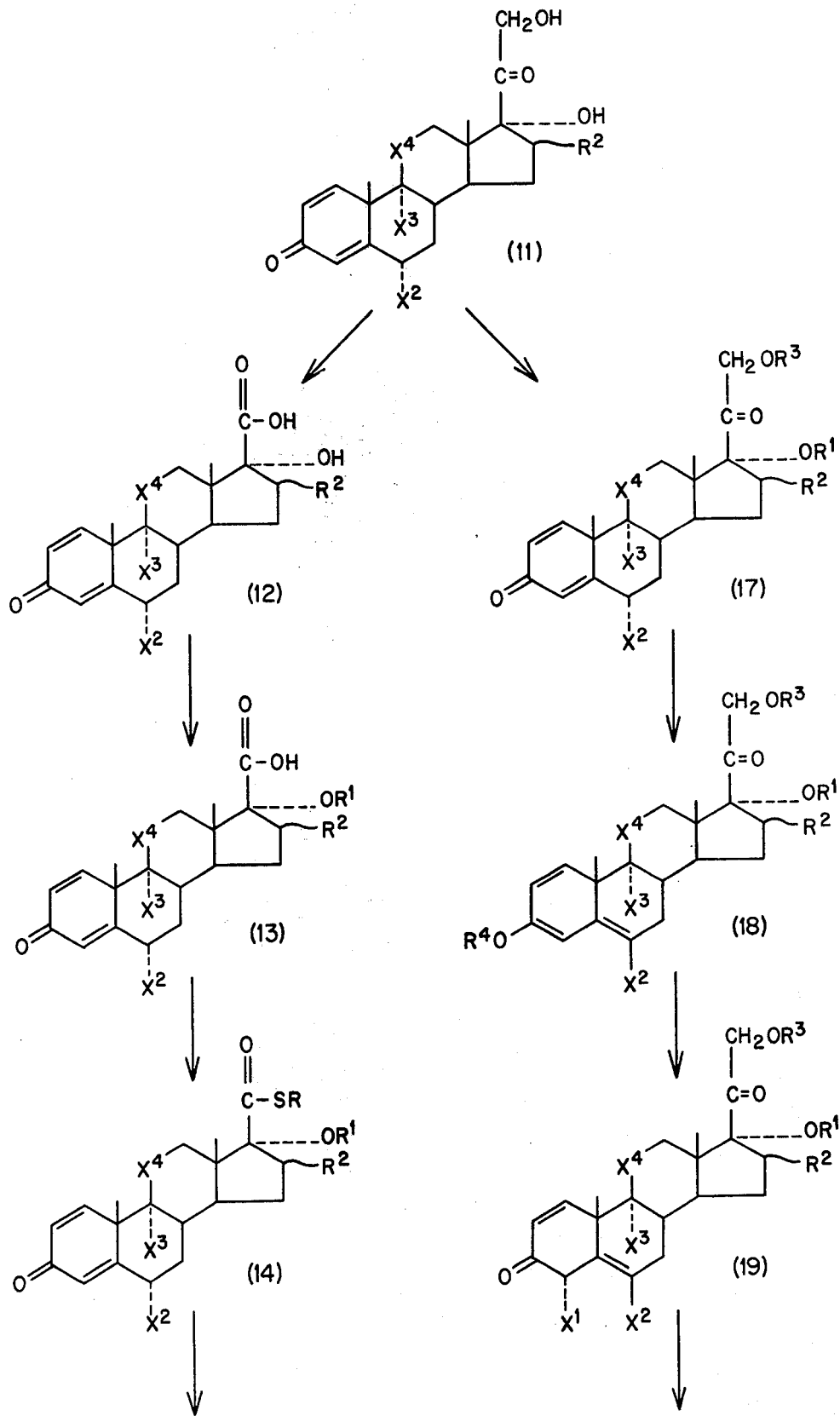
REACTION SEQUENCE B

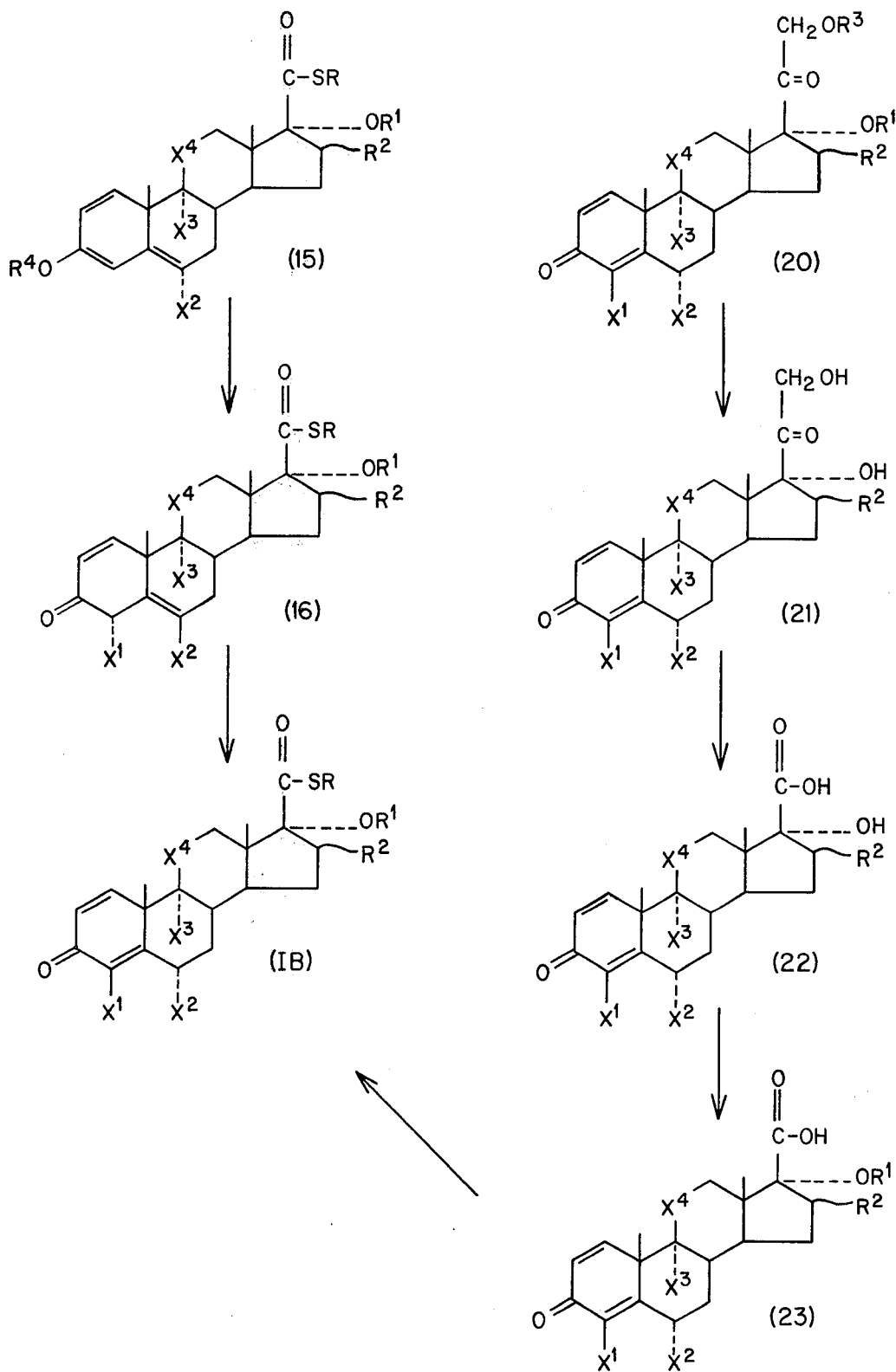
REACTION SEQUENCE B

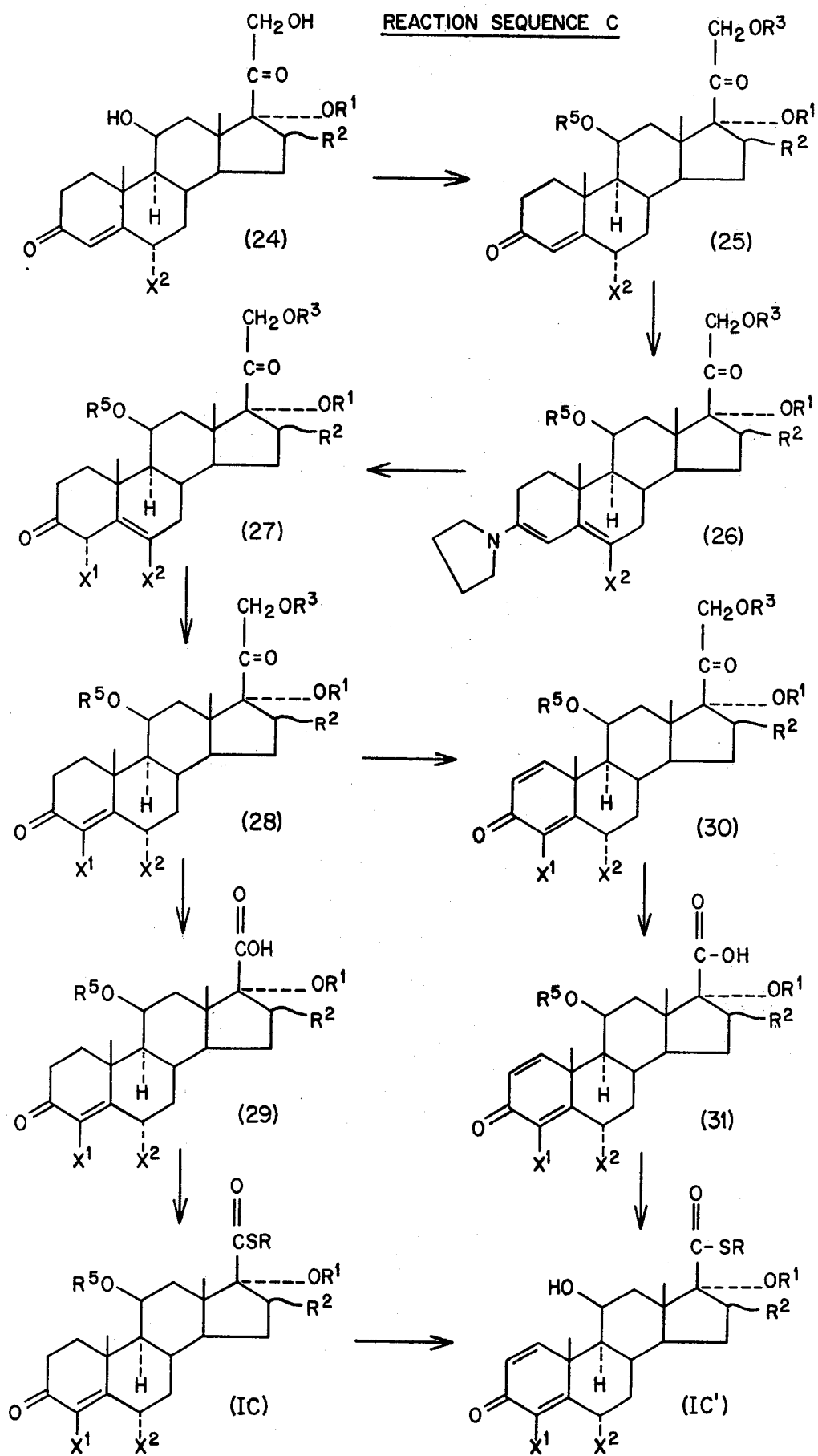

17 BETA-THIOCARBOXYLIC ACID ESTERS OF 4-HALO-3-OXOANDROST-4-ENES

BACKGROUND OF THE INVENTION

1. Field of the Invention

This invention relates to novel alkyl, benzyl or phenyl 3-oxoandrost-4-ene 17 beta-thiocarboxylates and the corresponding androsta-1,4-dienes. More specifically it relates to anti-inflammatory 16 alpha,17 alpha-acetonides and 17 alpha-hydroxy-16-methyl compounds which are substituted at the 4 position with fluoro, chloro or bromo and are optionally substituted at the 6 position with fluoro or chloro. The invention further relates to pharmaceutical anti-inflammatory compositions comprising a compound of the invention in combination with a pharmaceutically acceptable excipient. This invention even further relates to a process for the preparation of these novel compounds.

2. Prior Art

Certain 3-oxoandrost-4-ene 17 beta-carboxylic acids which are substituted at the 9 position with chlorine or fluorine and at the 11 position with keto or hydroxy or chloro group are known. See for example U.S. Pat. No. 3,828,080. It is known that 3-oxoandrost-4-ene 17 beta-carboxylic acids may be substituted at both the 9 alpha and 6 alpha positions with fluoro. See for example U.S. Pat. No. 3,636,010.

It is also known from U.S. Pat. No. 3,989,686 to Phillipps et al. of Glaxo that steroids of formula (II) wherein
- $R^1$ is H or $CH_3$;
- $R^2$ is H or $CH_3$;
- $R^3$ is H or, when $R^2$ is H, $C_{1-6}$ alkoxy, $C_{1-5}$ alkyl, thiocyanato or halogen;
- $R^4$ is H or $CH_3$;
- $R^5$ is $C_{1-6}$ alkyl optionally substituted by halo or $NR^6R^7$, where $R^6$ and $R^7$ are the same or different, $C_{1-6}$ alkyl or $R^6$ and $R^7$ together with N are morpholino, thiamorpholine or morpholino substituted with $C_{1-6}$ alkyl; and
- the dotted lines in the "A" ring represent an optional double bond at these positions. These compounds are useful as anesthetics.

Methyl 3 beta-acetoxyallothiol-cholonate and methyl 3 beta-acetoxy-etiothiolchol-5-enate are also known compounds. See, e.g., Jerger et al., Helv. Chem. Acta. 29, 684–92 (1946).

A heretofore unknown series of 3-oxoandrost-4-ene 17 beta-thiocarboxylates being substituted at the 4 position with fluoro, chloro or bromo and optionally substituted at the 6 position with fluoro or chloro has been discovered and is disclosed herein. The compounds exhibit good anti-inflammatory activity and few adverse side effects.

SUMMARY OF THE INVENTION

One aspect of this invention is a compound chosen from those represented by formula (I) wherein
- Z is sulfur;
- $X^1$ is fluoro, chloro or bromo;
- $X^2$ is fluoro, chloro or hydrogen;
- $X^3$ is fluoro, chloro, bromo or hydrogen;

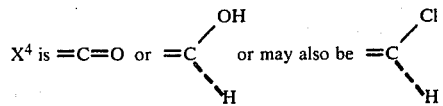

when $X^3$ may also be chloro;
- R is alkyl of 1 through 6 carbon atoms or phenyl or benzyl optionally substituted with 1 substituent chosen from the group consisting of alkyl of 1 through 4 carbon atoms, alkoxy of 1 through 4 carbon atoms and halo;
- $R^1$ is hydrogen or alkanoyl of 2 through 6 carbon atoms when $R^2$ is hydrogen, alpha-methyl or beta-methyl or $OR^1$ and $R^2$ together represent 16 alpha,17 alpha-isopropylidenedioxy; and
- the dotted line between C-1 and C-2 represents an optional double bond.

Another aspect of this invention is an anti-inflammatory pharmaceutical composition which comprises a suitable pharmaceutical excipient in combination with an effective amount of a compound chosen from those represented by formula (I), as defined above, wherein each of the substituents are as defined. Particularly valuable compounds of this composition are set forth hereafter.

Still another aspect of this invention is a process for treating an inflamed condition in mammals which comprises treating the afflicted mammal with an effective amount of a compound chosen from those represented by formula (I), above, wherein substituents are as defined above.

BRIEF DESCRIPTION OF THE DRAWINGS

Formula (I) sets forth a general structure of the compounds of this invention.

Formula (II) sets forth a general structure of certain prior art compounds of this invention.

Reaction Sequence A sets forth a process for preparing the 16 alpha,17 alpha-acetonide compounds of this invention represented by formula (IA) wherein $X^3$ is fluoro, chloro or bromo.

Reaction Sequence B sets forth a process for preparing the compounds of this invention represented by formula (IB) wherein $R^1$ is alkanoyl of 2–6 carbon atoms; $R^2$ is alpha-methyl, beta-methyl or hydrogen; and $X^3$ is fluoro, chloro or bromo.

Reaction Sequence C sets forth a process for preparing 11 beta-hydroxy compounds of this invention represented by formula (IC) and (IC') which are substituted at the 9 alpha- position with hydrogen.

DETAILED DESCRIPTION AND PREFERRED EMBODIMENTS

Compounds

In its broadest aspect, this invention is a compound chosen from those represented by formula (I) wherein
- Z is sulfur;
- $X^1$ is fluoro, chloro or bromo;
- $X^2$ is fluoro, chloro or hydrogen;
- $X^3$ is fluoro, chloro, bromo or hydrogen;

$X^4$ is =C=O or 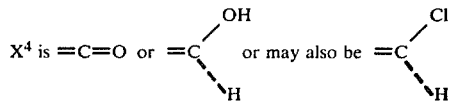 when $X^3$ is chloro;

R is alkyl of 1 through 6 carbon atoms or phenyl or benzyl optionally substituted with 1 substituent chosen from the group consisting of alkyl of 1 through 4 carbon atoms, alkoxy of 1 through 4 carbon atoms and halo;

$R^1$ is hydrogen or alkanoyl of 2 through 6 carbon atoms when $R^2$ is hydrogen, alpha-methyl or beta-methyl or $OR^1$ and $R^2$ together represent 16 alpha,17 alpha-isopropylidenedioxy;

the solid and broken lines between C-1 and C-2 represent a double or single bond.

One subgroup of the broad aspect of the invention comprises those compounds represented by formula (I) wherein $X^1$, $X^2$, $X^3$, $X^4$ and $R^1$ are as defined previously; R is alkyl of 1–6 carbon atoms, phenyl or benzyl; and $R^2$ is alpha-methyl. A subdivision of this subgroup includes those compounds of formula (I) wherein $X^1$ and $X^2$ are independently fluoro or chloro; $X^3$ is hydrogen, fluoro or chloro;

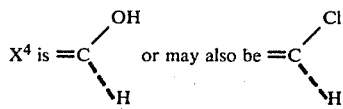

when $X^3$ is chloro; and R is alkyl of 1–2 carbon atoms (particularly methyl). Of the compounds of this subdivision, the preferred compounds are represented by formula (I) wherein $X^1$ and $X^2$ are both fluoro and R is methyl. Particularly preferred of these compounds are compounds wherein R is methyl, $X^1$, $X^2$ and $X^3$ are all fluoro and

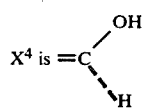

or compounds wherein R is methyl, $X^1$ and $X^2$ are both fluoro, $X^3$ is chloro and $X^4$ may also be

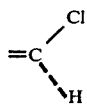

Another subgroup of the compounds of this invention includes those compounds represented by formula (I) wherein R is alkyl of 1–6 carbon atoms, phenyl or benzyl; $OR^1$ and $R^2$ together represent 16 alpha,17 alpha-isopropylidenedioxy;

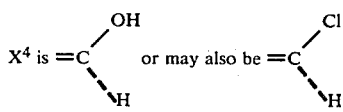

when $X^3$ is chloro; and $X^1$, $X^2$ and $X^3$ are as defined in the broadest aspect of the invention. A subdivision of this subgroup includes those compounds of formula (I) wherein $X^1$ and $X^2$ are independently fluoro or chloro; $X^3$ is hydrogen, fluoro or chloro;

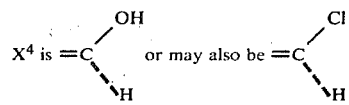

when $X^3$ is chloro; and R is alkyl of 1 or 2 carbon atoms (particularly methyl). Of the compounds of this subdivision, the preferred compounds are represented by formula (I) wherein $X^1$ and $X^2$ are both fluoro. Particularly preferred of these latter compounds are those wherein R is methyl, $X^1$, $X^2$ and $X^3$ are all fluoro and

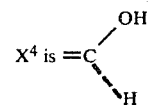

or those wherein R is methyl, $X^1$ and $X^2$ are both fluoro, $X^3$ is chloro and $X^4$ may also be

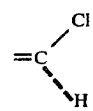

In defining the compounds of this invention the term "alkyl" includes both straight chain and branched alkyl groups, thus alkyl of 1–6 carbon atoms includes methyl, ethyl, n-propyl, isopropyl, n-butyl, isobutyl, t-butyl, pentyl, isoamyl, n-hexyl and the like. The phenyl and benzyl substituents may be substituted on the phenyl ring at the 2, 3 or 4 positions with one substituent such as alkoxy of 1–4 carbons (e.g., methoxy, ethoxy, n-propoxy, t-butoxy and the like), alkyl of 1–4 carbons (e.g., methyl, ethyl, isopropyl, n-propyl, t-butyl, n-butyl, etc.), or a halo such as fluoro, chloro, bromo or iodo. Preferably the substitution is at the 2 or 4 positions.

The term "alkanoyl" refers to a radical of the formula

wherein $R^4$ is alkyl of 1–5 carbon atoms and includes e.g., acetyl, propionyl, butyryl, valeryl, caproyl, and the like.

In naming the compound of this invention the substituents present on the androstane ring shall be included alphabetically and the compounds shall be alkyl (or phenyl or benzyl) 17 beta-thiocarboxylates. For example, if in formula (I), above, $X^1$ and $X^2$ are fluoro, $X^3$ and $X^4$ are chloro, R is methyl, $R^1$ is acetoxy and $R^2$ is alpha-methyl the name is methyl 17 alpha-acetoxy-9 alpha,- 11 beta-dichloro-4,6 alpha-difluoro-16 alpha-methyl-3-oxo-androsta-1,4-diene-17 beta-thiocarboxylate. If, on the other hand, R is hydrogen but $X^1$, $X^2$, $X^3$, $X^4$, $R^1$ and $R^2$ are the same the compound is named 17 alpha-acetoxy-9 alpha,11 beta-dichloro-4,6 alpha-difluoro-16 alpha-methyl-3-oxoandrosta-1,4-diene 17 beta-thiocarboxylic acid.

Compound Preparation

The compounds of the invention may be prepared by any convenient method and in most cases they can be prepared by conventional techniques. They may, for example, be prepared by reacting a reactive derivative of an appropriate androsta-1,4-diene 17 beta-carboxylic acid with a molar excess (about 1.05 to about 5 molar equivalents based on the steroid) of an alkali metal salt of a compound of the formula RSH where R is alkyl, benzyl or phenyl. Representative alkali metal salts include sodium methyl sulfide, sodium ethyl sulfide, sodium benzyl sulfide, sodium phenyl sulfide, potassium methyl sulfide, and the like. The alkali metal salt can be reacted directly with the reactive derivative of the 17 beta-carboxylic acid, or the salt can be formed in situ by mixing an alkali metal hydride, such as sodium hydride or potassium hydride, with an alkyl, phenyl or benzyl sulfide. The thioesterification reaction readily takes place at temperature of about 10° to 100° C. (preferably at ambient temperature of about 20°–25° C.) in a suitable inert solvent such as dimethylformamide, diethylformamide, dimethylacetamide, and the like.

The reactive derivative of the 17 beta-carboxylic acid may be an acid chloride, but is preferably a mixed anhydride, such as the dialkyl phosphate ester prepared by reacting a dialkyl (1-4 carbons) chlorophosphate (e.g., diethyl chlorophosphate) with the appropriate 17 beta-carboxylic acid in an inert solvent such as tetrahydrofuran (THF) under an inert atmosphere (nitrogen) at temperatures of about 10°–50° C., preferably about 20°–25° C.

Several overall processes may be employed to prepare the compounds of this invention from known pregnanes. These are outlined in Reaction Sequence A–C.

Reaction Sequence (A) sets forth essentially a three-part process for the preparation of the 16 alpha, 17 alpha-acetonide compounds of this invention, the parts of which may be carried out in any order. One part is to eliminate the 21 carbon atom from a suitable 21-hydroxy 6 alpha-fluoro pregnane, or a suitable ester thereof; another part is to fluorinate, chlorinate or brominate at the 4-position, and the third part is to form the thiocarboxylate. In Reaction Sequence (A), R is a suitable alkyl, benzyl or phenyl group as defined in the broadest aspect of the invention; $R^3$ is alkanoyl of 2-6 carbons; $X^4$ is

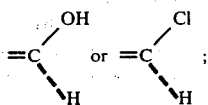

$R^4$ is methyl or ethyl; and $X^3$ is fluoro, chloro or bromo. In the Reaction Sequence, the fluorination (chlorination or bromination) is a three-step process, the elimination of the 21-carbon atom is essentially a one-step process, and the thioesterification is a one-step process.

The elimination of a 21 carbon atom from a suitable pregnane, represented by formulas (1) or (9), is readily accomplished by any means known in the art such as using sodium hypobromite or hypoiodite as taught in U.S. Pat. No. 2,769,822 or by using sodium periodate. Preferably, however the elimination of the 21-carbon atom is carried out by using an alkali metal carbonate in alcohol in the presence of oxygen as described in PA-application Ser. No. 893,642 filed Apr. 5, 1978. In the latter case the reaction is carried out at room temperature and atmospheric pressure while the source of oxygen is preferably air. Generally the reaction will be completed within less than 72 hours with a constant stream of air being bubbled into a stirred reaction mixture to give a compound of formula (2) or (10), respectively.

Once a compound represented by formula (2) or (10) is obtained it is readily thioesterified by methods discussed hereinbefore to give the 17 beta-thiocarboxylate represented by formula (3) or (IA), respectively.

The compound represented by formula (3), in turn, is fluorinated, chlorinated or brominated (collectively referred to as halogenated) at the 4-position using the three step halogenation technique.

The first step of the halogenation process is performed by reacting a compound of formula (3) to form a compound of formula (4) wherein $R^4O$ is methoxy or ethoxy. This is carried out by reacting, for example, a large molar excess of trimethyl orthoformate in methanol or triethyl orthoformate in ethanol in the presence of a catalytic amount (i.e., less than 5% by weight) of a suitable acid catalyst such as fuming sulfuric acid at reflux temperature or less. About 50°–55° C. is preferred. Generally the molar ratio of the orthoformate to steroid is about 10:1 to about 30:1. Once the reaction is complete a base is added to neutralize the acid and the resulting product represented by formula (4) is recovered and purified using methods well known in the art such as recrystallization, chromatography, etc.

The compound represented by formula (4) is then halogenated using perchloryl fluoride ($ClO_3F$) or trifluoromethoxy fluoride ($CF_3OF$) as a fluorinating agent, a source of positive chlorine such as N-chlorosuccinimide, dichlorohydantoin, etc., as a chlorinating agent, or N-bromosuccinimide as a brominating agent to form the 3-keto-4 alpha-fluoro (chloro or bromo) steroid represented by formula (5).

In the case of $ClO_3F$, which is a gas, an approximately equimolar amount, i.e., about 1 to 1.1 moles $ClO_3F$ per mole compound of formula (4) is metered into a mixture of the compound in a solution which is a major amount of acetone, preferably 90% by volume, and a minor amount water, preferably about 10%, over a period of about 1-3 hours at about −75° to 20° C., preferably starting at about −75° C. and allowing the reaction mixture to slowly warm to ambient temperatures. Dichlorohydantoin or N-bromosuccinimide are reacted using a solvent such as acetone and water or tetrahydrofuran and water to dissolve the reactants and adding the halogenating solution to the compound in a similar solvent at about −50° C. to about 50° C.

The resulting compound of formula (5), in turn, is recoverd and reacted with a suitable base such as an alkali metal carbonate, e.g., potassium carbonate, in a suitable oxygenated hydrocarbon solvent such as an alkanol, e.g., methanol, in an inert atmosphere, to rearrange the pregna-1,5diene to form the desired 4-fluoro (4-chloro or 4-bromo)-3-oxopregna-1,4-diene represented by formula (IA).

It will be appreciated that a compound represented by formula (7) is readily halogenated to a compound of formula (9) through intermediates (7) and (8) by the same halogenation process as discussed above.

Once the desired 3-keto-androsta-1,4-diene represented by formula (IA) is obtained, the compound may be readily selectively hydrogenated across the 1-2 bond by any of the means known in the art to obtain the corresponding 3-keto-androst-4-ene.

Turning now to Reaction Sequence B, a process is shown for preparing the compounds of this invention wherein $R^1$ is alkanoyl, $R^2$ is alpha-methyl, beta-methyl or hydrogen; $X^3$ is fluoro, chloro or bromo; and $X^1$, $X^2$, $X^4$ and R are defined hereinbefore in the broad aspect of this invention. The process is in essence the same as that set forth in Reaction Sequence A except that an alkanoyl, $R^1$, is introduced into formula (12) and (11) to form compounds of formulas (13) and (17), respectively. This is done by reacting a compound of formulas (12) or 11) with a suitable anhydride such as propionic anhydride, acetic anhydride, butyric anhydride, valeric anhydride, and the like in a suitable solvent such as a lower alkanol (e.g., methanol, ethanol) or an excess of the anhydride itself in the presence of an organic base such as an amine (e.g., pyridine, triethylamine). In the case where $X^4$ is

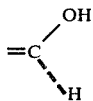

preferably sufficient anhydride (e.g., acetic anhydride) is reacted in the presence of ethylamine and dimethylaminopyridine to form an 11 beta,17 alpha,21-triacetoxy steroid of formula (17). The resulting compound is then halogantated at the 4-position as discussed for Reaction Sequence A, the 21 carbon is removed as discussed above and finally the alkyl, phenyl or benzyl 17 beta-thiocarboxylate (IB) is formed.

In the case where the compound represented by formula (20) is an 11 beta,17 alpha,21-triactoxy compound, it is preferably first hydrolyzed using a weak base such as potassium carbonate in methanol at temperatures of about 10°-50° C., e.g., ambient temperature, to form the 11 beta,17 alpha,21-trihydroxy compound of formula (21). This compound is reacted with potassium carbonate and oxygen to form a compound of formula (22) which is then alkanoated at 17 alpha using propionic anhydride as discussed before to form a compound of formula (23). This then is reacted to form a compound of this invention represented by formula (IB) as discussed hereinbefore.

Alternatively, if the 21-carbon is removed first to form (12). This compound is then reacted with a suitable anhydride to form a compound of formula (13) which, in turn, is thioesterified to form a compound of formula (14) then halogenated to give the compound of the invention represented by formula (IB).

Again, once the 1,4-diene represented by formula (IB) is obtained, it is readily converted to the corresponding 4-ene by methods well known in the art such as hydrogenating with tris (triphenylphosphine) chlororhodium in ethanol.

If $X^3$ in the compound represented by formula (I) is hydrogen, then Reaction Sequence C is followed where the starting compound is represented by formula (24), wherein $OR^1$ and $R^2$ may be 16 alpha,17 alpha-actonide or $R^1$ is H or alkanoyl when $R^2$ is alpha-methyl, beta-methyl or hydrogen; $R^3$ is alkanoyl; $X^1$ is fluoro, chloro or bromo; and $X^2$ is fluoro, chloro or hydrogen.

In the first step, if appropriate, the compound of formula (24) is alkanoated at 17 alpha-, 11 beta- and 21 as discussed hereinbefore. Thereafter the 4-halogenation proceeds through an intermediate enamine represented by formula (26) which is formed by reacting the compound of formula (25) with a suitable amine such as pyrrolidine, in an inert organic solvent such as benzene or methanol at temperatures of about 10°-100° C., preferably about 50°-55° C.

The other steps in the reaction sequence immediately above are in essence discussed hereinbefore. The conversion of a compound of formula (28) to one of formula (30) or (IC) to (IC') is performed by means known in the art such as by refluxing in dioxane and 2,3-dichloro-5,6-dicyano-1,4-benzoquinone for a sufficient period (generally less than 24 hours) to form the compound of formula (30) or (IC').

The starting materials for Reaction Sequences (A)–(C), represented by formulas (1), (11) or (24) are readily prepared by starting with compounds known in the art and proceeding according to known methods.

Suitable 21-hydroxy-3,20-dioxopregn-4-en or pregna-1,4-dienes include known compounds such as corticosterone, hydrocortisone, prednisolone, betamethasone, dexamethasone, paramethasone, triamcinolone acetonide, fluocinolone acetonide, and the like. By following procedures generally known in the art steroids of a relatively simple structure can be converted to other structures as desired.

For example, the 6-fluoro or 6-chloro starting steroids can be prepared from known steroids such as 7-alpha-hydroxy-progesterone or hydrocortisone by treating a 3-methoxy-pregna-3,5-diene (prepared by reacting a 3-keto-pregn-4-ene with triethyl orthoformate in methanol) with perchloryl fluoride in dimethylformamide or dichlorohydantoin in acetone.

Other 6-fluoro starting steroids employed in the present process to prepared the novel 17 beta-thiocarboxylic acid derivatives of this invention are described in the literature and in United States and foreign patents. For example, see U.S. Pat. Nos. 2,983,737, 2.983,839, 3,053,838, 3,057,858, 3,124,251, 3,126,375, 3,201,391 and 3,248,389.

The 9 alpha-fluoro, chloro or bromo group is introduced by treating a 9 beta, 11 beta-oxido steroid with hydrogen fluoride, hydrogen chloride or hydrogen bromide respectively in an inert, nonaqueous, preferably anhydrous, solvent or mixture of such solvents. For example, see U.S. Pat No. 3,211,758 to Tarkoey wherein a hydrogen fluoride/-urea complex is employed. The 9 beta,11 beta-oxido steroid is prepared from the corresponding pregna-1,4,9-(11)-triene.

The pregna-1,4,9(11)-triene-3,20-diones or the corresponding 4,9(11)-dienes are known or can readily be prepared by treating a known 11-hydroxy steroid, such as prednisolone, 6 alpha-fluoro-prednisolone or the like, in dimethylformamide and pyridine and reacting with methanesulfonyl chloride with about 5 % sulfur trioxide at room temperature for 20-24 hours, then extracting with methylene chloride and recovering according to the process set forth in Example 3A of U.S. Pat. No. 3,009,933 to Robinson.

the pregna-1,4,9(11)-trienes or 4,9(11)-dienes are also converted to starting materials for Reaction Sequences (A), (B) or (C) by means known in the art. For example they are treated with chlorine according to the process of U.S. Pat. No. 3,009,933 to give the corresponding 9 alpha, 11 beta-dichloropregna-1,4-diene (i.e., $X^3$ is chloro and $X^4$ is

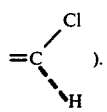

The 9 alpha-bromo-11 beta-hydroxy compound or the 9 alpha-chloro-11 beta-hydroxy compound is prepared by reacting the appropriate pregna-1,4,9(11) triene in dioxane with dibromohydantoin or dichlorohydantoin, respectively. This may be isolated and purified, or in turn, can be reacted with sodium hydroxide to give the corresponding 9 beta, 11 beta-epoxide which is then treated with HCl, HBr or HF as discussed above.

An 11 beta-hydroxy (9-unsubstituted) steroid is readily prepared from a 3-keto-6 alpha-substituted-pregna-1,4-diene or pregn-4-ene by methods well known in the art such as employing *Cunninghamella blakesleeana, Cunninghamella bainieri, Curvularia lunata,* or other suitable microrganisms in a suitable medium which selectively affords the desired 11 beta-hydroxy steroid.

The 16-methyl group is introduced by treating the corresponding 20-keto-16-pregnene with methyl magnesium bromide in the presence of cuprous chloride in an ether such as tetrahydrofuran. The 20-keto-16-pregnene steroid is prepared by preparing the 3,20 bis-semicarbazone of a 3,20-diketo-17 alpha-hydroxy steroid, treating it with glacial acetic acid and acetic anhydride and then allowing the resulting product to react with aqueous pyruvic acid.

The 17 alpha-hydroxy group is introduced in conjunction with the 16 beta-methyl group by first treating the corresponding 16-methyl-pregn-16-ene (which is prepared by treating the corresponding pregn-16-ene with diazomethane and then heating the resulting product to 180° C.) with hydrogen peroxide, in an aqueous basic media, then permitting the resulting 16,17-oxido-16-methyl steroid to react with hydrogen bromide in glacial acetic acid. The resulting 16,17-bromohydrin is hydrogenated wth the use of a palladium catalyst to afford the corresponding 16 beta-methyl-17-alpha-hydroxy derivative.

The 17 alpha-hydroxy group is introduced in conjunction with the 16 alpha-methyl by methods known in the art, such as the method described by Edwards et al. in the Journal of the American Chemical Society 82, 2318-22, 1960. In this process an appropriate 21-substituted 16 alpha-methylpregna-1,4-diene-3,2-dione is converted to 20-enol acetate by refluxing with acetic anhydride and freshly distilled acetyl chloride. The 20-enol acetate is recovered and reacted with monoperphthalic acid in ether and benzene to form the 17,20 epoxide which in turn is trated with methanol and aqueous potassium hydroxide to give the 16 alpha-methyl-17 alpha-hydroxy steroid which is isolated by means known in the art.

ADMINISTRATION AND FORMULATION

The compounds of this invention are useful for the relief of inflamed conditions in mammals, and more specifically are useful for relieving inflammatory manifestations of corticosteroid responsive dermatoses. Initial approximation of anti-inflammatory activity is done by following the procedure of McKenzie, S.W. and Stoughton, R.B., "Method for Comparing Percutaneous Absorption of Steroids" Arch Dermat, 86, 608 (1962) or modifications thereof.

Generally, the inflammatory manifestation in mammals, particularly humans, is combatted by treating the afflicted mammal with a therapeutically effective amount of the novel steroids of this invention, that is an amount which results in improvement of the inflamed condition. Preferably the steroids are first formulated to prepare a suitable pharmaceutical formulation, as discussed hereinafter, which is then placed in contact with the afflicted area. An effective amount will depend upon the particular condition and the mammal receiving the treatment but will vary between 0.001% to 10% by weight of the pharmaceutical composition and preferably will be between 0.01 and 1% by weight of the formulation. Using these levels in the formulation, a therapeutically effective, non-side effect producing amount, i.e., enough to effect an anti-inflammatory response, but not enough to adversely effect the recipient, is applied to the inflamed area.

The compounds of this invention not only have anti-inflammatory activity but also exhibit a low level of systemic activity, as measured by recognized laboratory assays. This allows for the application of an effective amount of the anti-inflammatory compounds with little adverse effect on the rest of the mammal's system.

The novel steroids of this invention may be formulated with suitable pharmaceutical excipients known in the art to form particularly effective anti-inflammatory compositions. Generally an effective amount of the steroid is about 0.001%w to about 10%w of the total formulated composition. The rest of the formulated composition will be about 90%w to about 99.999%w of suitable excipients which may include a pharmaceutically acceptable solvent and other pharmaceutically acceptable additives to form an effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, suppositories, aerosols, solutions or the like. Particularly suitable solvents include water, glycerine, propylene carbonate, and a glycol such as 1,2-propylene diol (i.e., propylene glycol), 1,3-propylene diol, polyethylene glycol having a molecular weight of from 100 to 10,000, dipropylene glycol, etc.; and mixtures of the aforementioned with each other.

A topical cream may be prepared as a semi-solid emulsion of oil in water or water in oil. A cream base formulation by definition is an emulsion which is a two-phase system with one liquid (for example fats or oils) being dispersed as small globules in another substance (e.g., a glycol-water solvent phase) which may be employed as the primary solvent for the novel steroids therein, the cream formulation may contain fatty alcohols, surfactants, mineral oil or petrolatum and other typical pharmaceutical adjuvants such as anti-oxidants, antiseptics, or compatible adjuvants. A typical cream base formulation is given in the following table:

| | |
|---|---|
| Water/glycol mixture (15% or more glycol) | 50-99 parts by weight |
| Fatty alcohol | 1-20 |
| Non-ionic Surfactant | 0-10 |
| Mineral oil | 0-10 |
| Typical pharmaceutical | 0-5 |

| | |
|---|---|
| adjuvants | |
| Active Ingredients | 0.001–10 |

The fatty alcohol, non-ionic surfactant, and other adjuvants are discussed in U.S. Pat. No. 3,934,013 to Poulsen which is incorporated herein by reference.

The novel steroids of this invention may also be formulated as ointments. A "classical" ointment is a semisolid anhydrous composition which may contain mineral oil, white petrolatum a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | |
|---|---|
| White petrolatum | 40–94 parts by weight |
| Mineral Oil | 5–20 |
| Glycol solvent | 1–15 |
| Surfactant | 0–10 |
| Stabilizer | 0–10 |
| Active Ingredients | 0.001–10.0 |

Other suitable ointment base formulations which employ propylene carbonate are described in U.S. Pat. No. 4,017,615 issued Apr. 12, 1977 by Shastri et al. entitled "Propylene Carbonate Ointment Vehicle" and U.S. Pat. No. 3,924,004 issued Dec. 2, 1975 by Chang et al. entitled "Fatty Alcohol-Propylene Carbonate-Glycol Solvent Cream Vehicle." As much of those applications as is pertinent is incorporated herein by reference. Following is a typical ointment base formulation containing propylene carbonate:

| | |
|---|---|
| Active Ingredients | 0.001–10.0 parts by weight |
| Propylene Carbonate | 1–10 |
| Solvent | 1–10 |
| Surfactant | 1–10 |
| White Petrolatum | 70–97 |

Suitable solvents, surfactants, stabilizers, etc. are discussed in U.S. Pat. No. 3,934,013 and such discussion is incorporated herein by reference.

A suitable "non-classical" anhydrous, water washable "ointment type" base is described in U.S. Pat. No. 3,952,930 to Katz and Neiman, and that patent is incorporated herein by reference. A representative composition of this invention utilizing such a base is as follows:

| | |
|---|---|
| Glycol solvent | 40–35 parts by weight |
| Fatty alcohol | 15–45 |
| Compatible plasticizer | 0–15 |
| Compatible coupling Agent | 0–15 |
| Penetrant | 0–20 |
| Active Ingredients | 0.001–10.0 |

PREPARATION I

This preparation sets forth a process for preparing compounds represented by formula (I) wherein
Z is oxygen;
$X^1$ is fluoro;
$X^2$ is fluoro, chloro or hydrogen;
$X^3$ is fluoro, chloro or bromo;

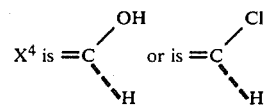

when $X^3$ is Cl;
R is hydrogen;
$R^1$ is alkanoyloxy of 2–6 carbon atoms; and
$R^2$ is hydrogen or methyl.

A. Ten grams (10 g.) of flumethasone is treated at room temperature with 50 ml of Et$_3$N and 50 ml of acetic anhydrid plus 2 g of dimethylaminopyridine. The mixture is heated on the steam bath for 5 hours. Examination of the reaction mixture by thin layer chromatography (TLC) analysis using 10% ethyl acetate/90% dichloromethane (DCM) shows the reaction to be complete. The mixture is cooled in an ice water bath, and slowly diluted with water up to a final volume of 2 liters. The semicrystalline precipitate so obtained is collected by filtration, washed with water, and dissolved in 200 ml of DCM, dried over anhydrous sodium sulfate, filtered and concentrated to dryness. The residue is dissolved in DCM and the solution is passed through a column of 100 g of silica gel eluting with 100% DCM, then 4% ethyl acetate in DCM. The homogeneous fractions are combined and concentrated to dryness. The residue is crystallized from CH$_2$Cl$_2$/MeOH and filtered. The filtrate is dried on the steam bath to give 11 beta,17 alpha,21-triacetoxy-6 alpha,9 alpha -difluoro-16 alpha-methylpregna-1,4-diene-3,20-dione.

Ten g of the triacetate prepared in this manner is treated with 150 mg of trimethylorthoformate and 50 ml of anhydrous methanol, using 5 ml of fuming sulfuric acid as catalyst. The reaction mixture is heated at 40°–50° C. for a period of 30 minutes, then 25 ml of triethylamine (TEA) is added, and the mixture concentrated under reduced pressure to dryness. The residue is dissolved into 200 ml of DCM, washed thrice with 50 ml of water, dried over anhydrous sodium sulfate, filtered, and the solvent removed under reduced pressure. The residue is dissolved in 25 mls of pyridine and treated at room temperature with 5 ml of acitic anhydride for a period of one hour. The reaction mixture is diluted slowly with 500 mls of water, stirred at room temperature for 4 hours. The precipitate so obtained is collected by filtration, washed with water, dissolved in 200 ml of DCM, dried over anhydrous sodium sulfate, filtered and concentrated to dryness. The residue is chromatographed over 100 g of silica gel in a DCM/hexane system to give 7.5 g of 11 beta,17 alpha,21-triacetoxy-6,9 alpha-difluoro-16 alpha-methyl-3-methoxypregna-1,3,5-triene-20-one, after concentration of the homogeneous fractions.

A mixture of 10 g of trienol ether prepared in this manner in 300 ml of 90% acetone/10% water, is treated at room temperature with a slow stream of perchloryl fluoride for a period of 45 minutes. The reaction mixture is diluted with 300 ml of water, and the acetone is eliminated under reduced pressure. The precipitate so obtained is extracted with DCM, washed thrice with 50 ml of water, dried over anhydrous sodium sulfate, and concentrated to dryness under reduced pressure. The residue is precolated through a column of 100 g silica gel eluting with a DCM/hexane system; increasing the polarity of the eluant to 100% DCM gradually. The homogeneous fractions containing 11 beta,17 alpha,21-triacetoxy-4 alpha,6,9 alpha-trifluoro-16 alpha-methyl-1,5-diene-3,20-dione are combined, concentrated to dryness to give 5.3 g of 11 beta,17 alpha,21-triacetoxy-4 alpha,6,9 alpha-trifluoro-16 alpha-methyl-1,5-diene-3,20-dione.

Ten g of 11 beta,17 alpha,21-triacetoxy-4 alpha,6,9 alpha-trifluoro-16 alpha-methylpregna-1,5-diene-3,20-dione prepared in this manner in 300 ml of methanol is treated at room temperature with 2 g of anhydrous potassium carbonate under nitrogen for 1 hour. The mixture is acidified by addition of 10 ml of glacial acetic acid; the mixture is diluted with 300 ml of water; and the methanol eliminated under reduced pressure, to leave a crystalline precipitate of 4 alpha,6,9 alpha-trifluoro-11 beta,17 alpha,21-trihydroxy-16 alpha-methylpregna-1,4-diene-3,20-dione Ten (10) g of 4,6 alpha,9 alpha-trifluoro-11 beta-17 alpha,21-trihydroxy-16 alpha-methylpregna-1,4-diene-3,20-dione in 300 ml of anhydrous methanol is treated with 30 g of anhydrous potassium carbonate at room temperature under stirring for a period of 24 hours while air is continuously bubbled through the reaction mixture. Methanol is added at intervals to maintain the original volume. The reaction mixture is diluted with 300 mls of water, and acidified with concentrated hydrochloric acid until a pH of 2 is obtained. The reaction mixture is concentrated under reduced pressure, until most of the methanol is eliminated. The mixture is cooled to room temperature, and the resulting crystalline precipitate is collected by filtration and air dried to yield 4,6 alpha,9 alpha-trifluoro-11 beta,17 alpha-dihydroxy-16 alpha-methyl-3-oxoandrosta-1,4-diene 17 beta-carboxylic acid.

Ten (10) g of 4,6 alpha,9 alpha-trifluoro-11 beta,17 alpha-dihydroxy-16 alpha-methyl-3-oxoandrosta-1,4-diene 17 beta-carboxylic acid is treated at room temperature with 50 ml of propionic anhydride and 40 mls of anhydrous pyridine. The mixture is stirred for one hour, then slowly diluted with water up to 2 liters while the mixture is cooled in an ice-water bath. The crystalline precipitate so obtained is collected by filtration, washed with water and dried, to give 4,6 alpha,9 alpha-trifluoro-11 beta-hydroxy-16 alpha-methyl-3-oxo-17 alpha-propionyloxyandrosta-1,4-diene 17 beta-carboxylic acid.

Similarly, by substituting an appropriate starting material for flumethasone the following compounds are prepared:

9 alpha,11 beta-dichloro-4,6 alpha-difluoro-16 alpha-methyl-3-oxo-17 alpha-propionyloxyandrosta-1,4-diene 17 beta-carboxylic acid;

9 alpha-bromo-4,6 alpha-difluoro-11 beta-hydroxy-16 alpha-methyl-3-oxo-17 alpha-propionyloyandrosta-1,4-diene 17 beta-carboxylic acid;

9 alpha-chloro-4,6 alpha-difluoro-11 beta-hydroxy-16 alpha-methyl-3-oxo-17 alpha-propionyloxyandrosta-1,4-diene 17 beta-carboxylic acid;

6-alpha,9-alpha-dichloro-4-fluoro-11-beta-hydroxy-16alpha-methyl-3-oxo-17alpha-propionyloxyandrosta-1,4-diene 17 beta-carboxylic acid;

9 alpha-bromo-6 alpha-chloro-4-fluoro-11-beta-hydroxy-16 alpha-methyl-3-oxo-17 alpha-propionyloxyandrosta-1,4-diene 17 beta-carboxylic acid;

4,9-alpha-difluoro-11 beta-hydroxy-16 alpha-methyl-2-oxo-17alpha-propionyloxyandrosta-1,4-diene 17 beta-carboxylic acid;

9 alpha-chloro-4-fluoro-11 beta-hydroxy-16alpha-methyl-3-oxo-17alpha-propionyloxyandrosta-1,4-diene 17 beta-carboxylic acid; and 9alpha-bromo-4-fluoro-11beta-hydroxy-16 alpha-methyl-3-oxo-17 alpha-propionyloxyandrosta-1,4-diene 17 beta-carboxylic acid.

C. By By substituting acetic anhydride, n-butyric anhydride, valeric anhydride, or caproic anhydride for propionic anhydride, the corresponding 17 alpha-acetates, n-butyrates, valerates or caproates are prepared.

D. The above compounds wherein $R^2$ is beta-methyl or H are prepared from the starting materials having at 16 beta-methyl substituent or being unsubstituted at 16.

PREPARATION II

This preparation sets forth a process for preparing compounds represented by formula (I) wherein
Z is oxygen;
$X^1$ is fluoro;
$X^2$ is fluoro, chloro or hydrogen;
$X^3$ is fluoro, chloro or bromo;

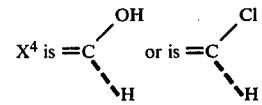

when $X^3$ is Cl;
R is hydrogen; and
$OR^1$ and $R^2$ together are 16 alpha,17alpha-acetonide.

A. By substituting fluocinolone acetonide for flumethasone in Preparation I, Part 1, and following in principle that process, 4,6 -alpha,9 alpha-trifluoro-11 beta-hydroxy-16 alpha,17 alpha-isopropylidenedioxy-2-oxoandrosta-1,4-diene 17 beta-carboxylic acid is prepared.

B. Similarly by substituting an appropriate starting material for fluocinolone acetonide in Part A of this preparation, other compounds are prepared such as 9 alpha,11 beta-dichloro-4,6 alpha-difluoro-16 alpha,-17 alpha-isopropylidenedioxy-3-oxoandrosta-1,4-diene 17 beta-carboxylic acid and the like.

PREPARATION III

This preparation sets forth a process for preparing compounds represented by formula I wherein $X^1$ is chloro or bromo and Z, $X^2$, $X^3$, $X^4$, R, $R^1$, and $R^2$ are the same as in Preparation I.

A. By following in principle the procedure of Preparation I, but substituting dichlorohydantoin or dibromohydantoin in aqueous acetone for perchloryl fluoride, the following compounds are prepared:

4-chloro-6alpha,9 alpha-difluoro-11 beta-hydroxy-16 alpha-methyl-3-oxo-17 alpha-propionyloxyandrosta-1,4-diene 17 beta-carboxylic acid; 4,9 alpha,11 beta-trichloro-6 alpha-fluoro-16 alpha-methyl-3-oxo-17 alpha-n-propionyloxyandrosta-1,4-diene 17 beta-carboxylic acid;

4-chloro-9 alpha-fluoro-11 beta-hydroxy-16 alpha-methyl-3-oxo-17 alpha-n-propionyloxyandrosta-1,4-diene 17 beta-carboxylic acid;

4,9alpha-dichloro-11 beta-hydroxy-16 alpha-methyl-3-oxo-17 alpha-propionyloxyandrosta-1,4-diene 17 beta-carboxlic acid; the analogous 4-bromo steroids; and the like.

B. By following in principle the procedure of Preparation I, Part B, other 17 alpha-alkanoyloxy derivatives of the compounds of Part A of this Example such as the 17 alpha-acetates, 17 alpha-n-butyryates 17 alpha-valerates or 17 alpha-caproates.

C. The compounds of Parts A and B of this preparation wherein $R^2$ is beta-methyl or H are prepared from starting materials having a 16 beta-methyl or being unsubstituted at the 16 position.

PREPARATION IV

This preparation sets forth a process for preparing compounds represented by formula (I) wherein $X^1$ is chloro or bromo and Z, $X^2$, $X^3$, $X^4$, R, $R^1$ and $R^2$ are the same as in Preparation II.

By following in principle the procedure of Preparation II, Parts A and B but substituting dichlorohydantoin or dibromohydantoin in aqueous acetone for perchloryl fluoride the following compounds are prepared:

4,9 alpha-dichloro-6 alpha-fluoro-11 beta-hydroxy-16 alpha,17 alpha-isopropylidenedioxy-3-oxoandrosta-1,4-diene 17 beta-carboxylic acid;

4-chloro-6 alpha,9 alpha-difluoro-11 beta-hydroxy-16 alpha,17 alpha-isopropylidenedioxy-3-oxoandrosta-1,4-diene 17 beta-carboxylic acid;

4,9 alpha,11 beta-trichloro-6 alpha-fluoro-16 alpha,17 alpha-isopropylidenedioxy-3-oxoandrosta-1,4-diene 17 beta-carboxylic acid;

4,6 alpha, 9 alpha-trichloro-11 beta-hydroxy-16 alpha,-17 alpha-isopropylidenedioxy-3-oxoandrosta-1,4-diene 17 beta-carboxylic acid; the analogous 4-bromo steroids; and the like.

PREPARATION V

This preparation sets forth a process for preparing compounds represented by formula (I) wherein
$X^1$ is fluoro, chloro or bromo;
$X^2$ is fluoro, chloro or hydrogen;
$X^3$ is hydrogen;

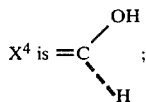

Z is oxygen;
R is hydrogen;
$R^1$ is alkanoyloxy of 2–6 carbons; and
$R^2$ is hydrogen, alpha-methyl or beta-methyl; and there is a single bond between C-1 and C-2.

A. Twenty g. of paramethasone (6 alpha-fluoro-16 alpha-methyl-prednisolone) are dehydrogenated according to methods discussed herein to give 6 alpha-fluoro-16 alpha-methyl-hydrocortisone.

Ten g. of a compound made according to the process of the preceding paragraph are added to a mixture of 10 ml methanol and about 5 g of pyrrolidine for a period of 5 to 24 hours. When TLC analysis shows the reaction is complete, the solvents are eliminated under reduced pressure to leave the enamine 6-fluoro-11-beta,17 alpha,21-trihydroxy-16 alpha-methyl-3-pyrrolidinyl-pregna-3,5-diene-20-one. The enamine is then purified by dissolving in a suitable organic solvent, filtering and recrystallizing or by column chromatography using alumina.

One g of a purified "enamine" from the previous step is dissolved in about 20 ml pyridine and the resulting solution is cooled to 0° C. A current of perchloryl fluoride is slowly bubbled into the stirred mixture and the reaction is monitored by TLC analysis. When analysis indicates the reaction is complete, the mixture is concentrated under reduced pressure to give a crude residue of 4 alpha, 6-difluoro-11 beta, 17 alpha, 21-trihydroxy-16 alpha-methylpregna-5 -ene-3,20-dione. The crude product is purified by recrystallization from a suitable solvent or by chromatography on silica gel.

One-half (0.5) g of the compound prepared according to the previous paragraph is dissolved in 20 ml of ethanol under a nitrogen atmosphere. A catalytic amount (approximately 20% of an equivalent based on the steroid) of anhydrous potassium carbonate is added, and the mixture stirred at room temperature for 1 to 5 hours while the reaction is monitored by TLC analysis. When the analysis indicates that the reaction is complete, glacial acetic acid is added to neutralize the potassium carbonate. Then the mixture is concentrated under reduced pressure to a small volume and diluted with water, to give a crystalline precipitate of 4,6 alpha-difluoro-11 beta, 17 alpha, 21-trihydroxy-16 alpha-methylpregn-4-ene-3,20-dione.

250 Mg of the resulting product in turn is mixed with 10 ml methanol and 50 mg anhydrous potassium carbonate and stirred at ambient temperature and atmospheric pressure while a current of air is slowly bubbled through the reaction mixture for 22 hours. Methanol is added at periodic intervals to maintain a constant volume. The reaction mixture is diluted with water to give a total volume of 300 ml, then concentrated hydrochloric acid is added slowly while stirring until a pH of 2 is obtained. The resulting crystalline precipitate is collected by filtration and air dried to give 4,6 alpha-difluoro-11 beta,17 alpha-dihydroxy-16 alpha-methyl-3-oxoandrost-4-ene-17 beta-carboxylic acid.

Similarly, by following in principle the procedure of this Preparation, above, but substituting dichlorohydantoin or N-bromosuccinimide for perchloryl fluoride, the following compounds are obtained:

4-chloro-6 apha-fluoro-11 beta, 17 alpha-dihydroxy-16 alpha-methyl-3-oxoandrost-4-ene 17 beta-carboxylic acid; and 4-bromo-6 alpha-fluoro-11 beta, 17 alpha-dihydroxy-16 alpha-methyl-3-oxoandrost-4-ene 17 beta-carboxylic acid.

B. By reacting each of the resulting products with acetic anhydride, propionic anhydride, n-butyric anhydride, valeric anhydride or caproic anhydride as discussed in Parts A and C of Preparation I, the corresponding 17 alpha-acetate, -propionate, -n-butyrate, valerate and caproate are preprepared.

C. The compounds of Part A and B of this preparation wherein $R^2$ at the 16 position is 16 beta-methyl or hydrogen are prepared from the starting materials having a 16 beta-methyl substituent or being unsubstituted at 16.

PREPARATION VI

This preparation sets forth a process for preparing compounds of formula (I) wherein $OR^1$ and $R^2$ together are 16 alpha,17 alpha-isopropylidenedioxy and $X^1$, $X^2$, $X^3$, $X^4$, Z and R are the same as in Preparation V.

A. By following in principle the process of Preparation V, Part A but substituting 6 alpha-fluoro-11 beta-hydroxy-16 alpha,17 alpha-isopropylidenedioxypregna-1,4-diene-3,20-dione for paramethasone, 4,6-alpha-difluoro-11 beta-hydroxy-16 alpha,17 alpha-isopropylidenedioxy-3-oxo-androst-4-ene 17 beta-carboxylic acid is prepared.

By substituting dichlorohydantoin or dibromohydantoin for perchloryl fluoride in this procedure the following compounds are prepared:

4-chloro-6 alpha-fluoro-11 beta-hydroxy-16 alpha,17 alpha-isopropylidenedioxy-3-oxoandrost-4-ene 17 beta-carboxylic acid;

4-bromo-6 alpha-fluoro-11 beta-hydroxy-16 alpha,17 alpha-isopropylidenedioxy-3-oxoandrost-4-ene 17 beta-carboxylic acid.

Specific embodiments of the process for preparing compounds of this invention are found in the following Examples which are given by way of illustration only and are not be be interpreted as limiting the scope of the claims appended hereto.

EXAMPLE 1

This example sets forth a process for preparing compounds of this invention represented by formula (I) wherein Z is sulfur; R is alkyl, benzyl or phenyl; and $X^2$, $X^3$, $X^4$, $R^1$ and $R^2$ are defined in Preparation I.

A. Six hundred (600) mg of 4,6alpha,9 alpha-trifluoro-11 beta-hydroxy-16 alpha-methyl-3-oxo-17 alpha-propionyl-oxyandrosta-1,4-diene 17-beta-carboxylic acid (prepared as set forth in Preparation I), 8 milliliters (ml) of tetrahydrofuran (THF) and 0.2 ml triethylamine (TEA) are placed in a suitable reaction vessel. The mixture is stirred at room temperature under nitrogen and 240 mg of diethyl chlorophosphate (DCP:$(C_2H_5O)_2P(O)(Cl)$) in 8 ml of THF is added thereto. The reaction mixture is stirred under nitrogen at room temperature for six hours whereupon 0.04 ml of TEA is added followed by 0.05 g DCP in 3 ml of THF. The resulting mixture is stirred for an additional 17.5 hours. The resulting precipitate is filtered off and washed with 10 ml THF. A solution of 2.05 ml of a solution of 20 ml DMF, 0.758 g 57% sodium hydride and 0.86 methyl sulfide (MeS) is added to the filtrate and the resulting mixture is stirred for about 5.5 hours at which time another 1 ml of the DMF/NaH/MeS solution is added.

This mixture is poured into 200 ml ethyl acetate, washed twice with 200 ml water, washed with brine, dried over sodium sulfate, filtered, and the solvents removed by rotary evaporator to give a crude material containing methyl 4,6 alpha, 9 alpha-trifluoro-11 beta-hydroxy-16 alpha-methyl-3-oxo-17 alpha -propionyloxyandrosta-1,4-diene 17 beta-thiocarboxy-late. This solid is purified by recrystallizing with acetone/hexane.

B. Similarly, by following the above procedure in this example but substituting other starting materials from Preparation I for 4,6 alpha, 9 alpha-trifluoro-11 beta-hydroxy-16 alpha-methyl-3-oxo-17 alpha-propionyloxyandrosta-1,4-diene 17 beta-carboxylic acid and/or other alkyl, benzyl or phenyl sulfides for methyl sulfide, other compounds of this invention are prepared, such as methyl 9 alpha, 11 beta-dichloro-4,6 alpha-difluoro-16 alpha-methyl-3-oxo-17 alpha-propionyloxyandrosta-1,4-diene 17 beta-thiocarboxylate;

ethyl 17 alpha-acetoxy 4,6 alpha, 9 alpha-trifluoro-11 beta-hydroxy-16 alpha-methyl-3-oxo-androsta-1,4-diene 17 beta-thiocarboxylate;

isopropyl 17 alpha-butyrloxy-4,6 alpha, 9 alpha-trifluoro-11 beta-hydroxy-16 alpha-methyl-3-oxoandrosta-1,4-diene17 beta-thiocarboxylate;

ethyl 9 alpha,11 beta-dichloro-4,6 alpha-difluoro-16 alpha-methyl-3-oxo-17 alpha-propionyloxyandrosta-1,4-diene 17 beta-thiocarboxylate;

methyl 9 alpha-chloro-4-fluoro-11 beta-hydroxy-16 alpha-methyl-3-oxo-17 alpha-n-propionyloxyandrosta-1,4-diene 17 beta-thiocarboxyate;

benzyl 4,6 alpha,9 beta-trifluoro-11 beta-hydroxy-16 alpha-methyl-3-oxo-17 alpha-propionyloxyandrosta-1,4-diene 17 beta-thiocarboxylate;

phenyl-4,6 alpha,9 alpha-trifluoro-11 beta-hydroxy-16 alpha-methyl-3-oxo-17 alpha-propionyloxyandrosta-1,4-diene 17 beta-thiocarboxylate;

4-chlorobenzyl 17 alpha-acetoxy-4,6 alpha,9 alpha-trifluoro-11 beta-hydroxy-16 alpha-methyl-3-oxoandrosta-1,4-diene 17 beta-thiocarboxylate; and the like.

EXAMPLE 2

This example sets forth a process for preparing compounds of this invention represented by formula (I) wherein Z is sulfur; R is alkyl, benzyl or phenyl; and $X^1$, $X^2$, $X^3$, $X^4$, $R^1$ and $R^2$ are as defined in Preparation II.

A. By following in principle the process of Example 1, Part A, but substituting 4,6 alpha,9 alpha-trifluoro-11 beta-hydroxy-16 alpha,17 alpha-isopropylidenedioxy-3-oxo-androsta-1,4-diene 17 beta-carboxylic acid, prepared in the manner set forth in Part A of Preparation 1, for 4,6 alpha,9 alpha-trifluoro-11 beta-hydroxy-16 alpha-methyl-3-oxo-17 alpha-propionyloxyandrosta-1,4-diene 17 beta-carboxylic acid, the compound methyl 4,6 alpha,9 alpha-trifluoro11 beta-hydroxy-16 alpha,17 alpha-isopropylidenedioxy-3-oxoandrosta-1,4-diene 17 beta-thiocarboxylate.

B. By following in principle the process of Part A of this example but substituting other alkyl, benzyl or phenyl sulfides for methyl sulfide and other 16 alpha,17 alpha acetonides prepared according to the process of Preparation II, for 4,6 alpha,9 alpha-trifluoro-11 beta-hydroxy-16 alpha,17 alpha-isopropylidenedioxy-3-oxoandrosta-1,4-diene 17 beta-carboxylic acid, other compounds of this invention are prepared such as ethyl 4,6 alpha,9 alpha-trifluoro-11 beta-hydroxy-16 alpha,17 alpha-isopropylidenedioxy-3-oxoandrosta-1,4-diene 17 -beta-thiocarboxylate;

isopropyl 4,6 alpha,9 alpha-trifluoro-11 beta-hydroxy16 alpha,17 alpha-isopropylieedioxy-3-oxandrosta-1,4-diene 17 beta-thiocarboxylate;

benzyl 4,6 alpha,9 alpha-trifluoro-11 beta-hydroxy-16 alpha,17 alpha-isopropylidenedioxy-3-oxandrosta-1,4-diene 17 beta-thiocarboxylate;

phenyl 4,6 alpha,9 alpha-trifluoro-11 beta-hydroxy-16 alpha,17 alpha-isopropylidenedioxy-3-oxoandrosta-1,4-diene 17 beta-thiocarboxylate;

methyl 9 alpha,11 beta-dichloro-4,6 alpha-difluoro-16 alpha,17 alpha-isopropylidenedioxy-3-oxoandrosta-1,4-diene thiocarboxylate;

ethyl 9 alpha,11 beta-dichloro-4,6 alpha-difluoro-16 alpha,17 alpha-isopropylidenedioxy-3-oxoandrosta-1,4-diene thiocarboxylate;

pentyl 9 alpha,11 beta-dichloro-4,6 alpha-difluoro-16 alpha-isopropylidenedioxy-3-oxoandrosta-1,4-diene thiocarboxylate;

benzyl 9 alpha,11 beta-dichloro-4,6 alpha-difluoro-16 alpha,17 alpha-isopropylidenedioxy-3-oxoandrosta-1,4-diene thiocarboxylate.

EXAMPLE 3

This example sets forth a process for preparing compounds of this invention represented by formula I wherein Z is sulfur; R is alkyl, phenyl or benzyl; and $X^1$, $X^2$, $X^3$, $X^4$, $R^1$ and $R^2$ are as defined in Preparation III.

By the following in principle the process of Example 1, but substituting an appropriate starting material from Preparation III for 4,6 alpha,9 alpha-trifluoro-11 beta-hydroxy-16 alpha-methyl-3-oxo-17 alpha-propionyloxyandrosta-1,4-diene 17 beta-carboxylic acid and optionally substituting other alkyl, phenyl or benzyl sulfides for methyl sulfide, other alkyl, phenyl or benzyl 17 beta-thiocarboxylates are prepared such as methyl 4,9 alpha,11 beta-trichloro-6 alpha-fluoro-16 alpha-methyl-3-oxo-17 alpha-propionyloxyandrosta-1,4-diene 17 beta-thiocarboxylate;

methyl 4-chloro-6 alpha,9 alpha-difluoro-11 beta-hydroxy-16 alpha-methyl-3-oxo-17 alpha-propionloxyandrosta-1,4-diene 17 beta-thiocarboxylate;

ethyl 17 alpha-acetoxy 4-chloro-6 alpha,9 alpha-difluoro-11 beta-hydroxy-16 alpha-methyl-3-oxoandrosta1,4-diene 17 beta-thiocarboxylate;

benzyl 4,9 alpha,11 beta-trichloro-6 alpha-fluoro-16 alpha-methyl-3-oxo-17 alpha-propionyloxyandrosta-1,4-diene 17 beta-thiocarboxylate;

phenyl 17 alpha-butyrloxy-4,9 alpha,11 beta-trichloro6 alpha-fluoro-16 alpha-methyl-3-oxoandrosta-1,4-diene 17 beta-thiocarboxylate;

n-propyl-4-chloro-6 alpha,9 alpha-difluoro-11 beta-hydroxy-16 alpha-methyl-3-oxo-17 alpha-propionyloxyandrosta-1,4-diene 17 beta-thiocarboxylate;

n-hexyl 4,9 alpha,11 beta-trichloro-6 alpha-fluoro-16 alpha-methyl-3-oxo-17 alpha-propionyloxyandrosta-1,4-diene 17 beta-thiocarboxylate;

n-pentyl 17 alpha-acetoxy-4-chloro-6 alpha,9 alpha-difluoro-11 beta-hydroxy-16 alpha-methyl-3-oxoandrosta-1,4-diene 17 beta-thiocarboxylate; and the like.

EXAMPLE 4

This example sets forth a process for preparing compounds of this invention represented by formula (I) wherein Z is sulfur; R is alkyl, benzyl or phenyl; and $X^1$, $X^2$, $X^3$, $X^4$, $OR^1$ and $R^2$ are defined in Preparation IV.

By following in principle the process of Example 2 but substituting an appropriate 16 alpha,17 alpha-acetonide for 4,6 alpha,9 alpha-trifluoro-11 beta-hydroxy-16 alpha,-17 alpha-isopropylidenedioxy-3-oxoandrosta-1,4-diene 17 beta-carboxylic acid and optionally substituting other alkyl, phenyl or benzyl sulfides for methyl sufide, other compounds of this invention are prepared such as methyl 4-chloro-6 alpha,9 alpha-difluoro-11 beta-hydroxy-16 alpha,17 alpha-isopropylidenedioxy-3-oxoandrosta-1,4-diene 17 beta-thiocarboxylate;

ethyl 4-chloro-6 alpha,9 alpha-difluoro-11 beta-hydroxy-16 alpha,17 alpha-isopropylidenedioxy-3-oxoandrosta-1,4-diene 17 beta-thiocarboxylate;

phenyl 4-chloro-6 alpha,9 alpha-difluoro-11 -beta-hydroxy-16 alpha,17 alpha-isopropylidenedioxy-3-oxoandrosta-1,4-diene 17 beta-thiocarboxylate;

methyl 4,9 alpha,11 beta-trichloro-6 alpha-fluoro-16 alpha,17 alpha-isopropylidenedioxy-3-oxoandrosta-1,4-diene 17 beta-thiocarboxylate;

ethyl 4,9 alpha,11 beta-trichloro-6 alpha-fluoro-16 alpha,17 alpha-isopropylidenedioxy-3-oxoandrosta-1,4-diene 17 beta-thiocarboxylate;

isopropyl 4,9 alpha,11 beta-trichloro-6 alpha-fluoro16 alpha,17 alpha-isopropylidenedioxy-3-oxoandrosta-1,4-diene 17 beta-thiocarboxylate;

benzyl 4,9 alpha,11 beta-trichloro-6 alpha-fluoro-16 alpah,17 alpha-isopropylidenedioxy-3-oxoandrosta-1,4-diene 17 beta-thiocarboxylate.

EXAMPLE 5

This example sets forth a process for preparing the compounds of this invention represented by formula (I) wherein Z is sulfur; $X^3$ is hydrogen; $X^4$ is

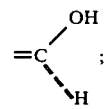

R is alkyl, benzyl, or phenyl; and $X^1$, $X^2$, $R^1$ and $R^2$ are defined in Preparation V.

By following in principle the process of Example I, but substituting an appropriate starting material from Preparation V for 4, 6 alpha, 9 alpha, trifluoro-11 beta-hydroxy-17 alpha-methyl-3-oxo-17 alpha-propionyloxyandrost-1,4-diene 17 beta-carboxylic acid and optionally substituting other alkyl, phenyl or benzyl sulfides for methyl sulfide, other alkyl, phenyl or benzyl 17 beta-thio carboxylates are prepared such as methyl 4-chloro-6 alpha-fluoro-11 beta-hydroxy-16 alpha-methyl-3-oxo-17 alpha-propionyloxyandrost-4-ene 17 beta-thiocarboxylate;

ethyl 4,6-alpha-difluoro-11 beta-hydroxy-16 alpha-methyl-3-oxo-17 alpha-propionyloxyandrost-4-ene 17 beta-thiocarboxylate;

n-propyl 4-fluoro-11 beta-hydroxy-16 alpha-methyl-3-oxo-17 alpha-propionyloxyandrost-4-ene 17 beta-thiocarboxylate;

n-pentyl 4,6 alpha-difluoro-11 beta-hydroxy-16 alpha-methyl-3-oxo-17 alpha-propionyloxyandrost-4-ene 17 beta-thiocarboxylate;

benzyl 4,6 alpha-difuoro-11 beta-hydroxy-16 alpha-methyl-3-oxo-17 alpha-propionyloxyandrost-4-ene 17 beta-thiocarboxylate;

phenyl 4,6 alpha-difluoro-11 beta-hydroxy-16 alpha-methyl-3-oxo-17 alpha-propionyloxyandrost-4-ene 17 beta-thiocarboxylate; and the like.

EXAMPLE 6

This example sets forth a process for preparing compounds of this invention represented by formula (I) wherein Z is sulfur; R is alkyl, benzyl or phenyl; $X^3$ is hydrogen;

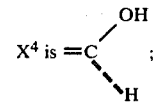

and $X^1$, $X^2$, $R^1$ and $R^2$ are defined in Preparation VI.

By following in principle the process of Example 2, but substituting an appropriate starting material from Preparation VI for 4, 6 alpha, 9 alpha-trifluoro-11 beta-hydroxy-16 alpha,17 alpha-isopropylidenedioxy-3-oxoandrosta-1,4-diene 17 beta-carboxylic acid and optionally substituting other alkyl, phenyl or benzyl sulfides for methyl sulfide, other alkyl, phenyl or benzyl 17 beta-thiocarboxylates are prepared such as methyl 4,6 alpha-difluoro-11 beta-hydroxy-16 alpha,17 alpha-isopropylidenedioxy-3-oxoandrost-4-ene 17 beta-thiocarboxylate;

ethyl 4,6 alpha-difluoro-11 beta-hydroxy-16 alpha,17 alpha-isopropylidenedioxy-3-oxoandrost-4-ene 17 beta-thiocarboxylate;

methyl 4-chloro-6 alpha-fluoro-11 beta-hydroxy-16 alpha,17 alpha-isopropylidenedioxy-3-oxoandrost-4-ene 17 beta-thiocarboxylate;

methyl 4-chloro-11 beta-hydroxy-16 alpha,17 alpha-isopropylidenedioxy-3-oxoandrost-4-ene 17 beta-thiocarboxylate;

methyl 4-bromo-6 alpha-fluoro-11 beta-hydroxy-16 alpha,17 alpha-isopropylidenedioxy-3-oxoandrost-4-ene 17 beta-thiocarboxylate; and the like.

EXAMPLE 7

This example sets forth an alternative method for preparing the compounds of this invention according to Reaction Sequence B through intermediates (13), (14), (15) and (17).

A mixture of 600 mg of 6 alpha,9 alpha-difluoro-11 beta-hydroxy-16 alpha-methyl-3-oxo-17 alpha-propionyloxyandrosta-1,4-diene 17 beta-carboxylic acid, 8 ml of THF and 0.2 ml of TEA are placed in a suitable reaction vessel and stirred at room temperature under a nitrogen blanket. A mixture of 0.24 g of DCP in 8 ml of THF is added over thirteen minutes. Stirring is continued for about six hours at which time 0.04 ml TEA is added, followed by 0.05 g DCP in 3 ml THF. The mixture is stirred for about 18 hours and the resulting precipitate is filtered off, then washed with 10 ml of THF. 2.05 Ml of a solution made from 20 ml dimethylformamide (DMF), 0.758 g 57% sodium hydride and 0.86 g methyl sulfide (DMS) is added to the reaction mixture. The resulting mixture is stirred for about 5½ hours when 1 additional ml of the DMS solution is added and stirring is continued for another hour and one half. The resulting mixture is poured into 200 ml of ethyl acetate, washed twice with 200 ml of water, washed with brine once, then dried overnight in a refrigerator over sodium sulfate, filtered to remove any solids, and finally the solvent is removed on a rotary evaporator. This results in 0.235 g crude material which is then recrystallized from an acetone/hexane mixture to yield 54.3 mg of methyl 6 alpha,9 alpha-difluoro-11 beta-hydroxy-16 alpha-methyl-3-oxo-17 alpha-propionyloxyandrosta-1,4-diene 17 beta-thiocarboxylate, m.p. 305°–308° C.

Six g of a compound prepared in this manner are mixed with 72 ml of trimethylorthoformate and 24 ml of anhydrous methanol along with 0.3 ml fuming sulfuric acid. The mixture is heated at 50° C. about 30 minutes at which time TLC using a 35% ethyl acetate-65% hexane system shows the reaction to be complete. Ten ml of triethylamine is added and the solvents are eliminated by vacuum evaporation. The residue is dissolved in 30 ml of methanol and slowly diluted with water whereupon crystals form. When a total volume of 2 liters is obtained, the crystalline precipitate is collected by filtration.

The resulting wet cake is dissolved in 300 ml of acetone with 30 ml of water and a stream of ClO$_3$F is slowly passed through the resulting solution for 10 minutes. TLC analysis of the reaction mixture using 35% ethyl acetate-65% hexane shows the reaction to be complete. The mixture is diluted with 100 ml of water, and the acetone is eliminated under reduced pressure. The remaining liquid mixture is diluted to 1 liter with water while a semi-crystalline precipitate forms. The precipitate is collected by filtration, dissolved in DCM the water layer separated and the DCM solution dried over anhydrous sodium sulfate and filtered. The resulting filtrate is percolated through 70 g of silica while eluting with 100% DCM. The 100% DCM is collected, then the combined eluates are concentrated to dryness and the resulting residue is dissolved in about 10 ml of methanol and diluted slowly with watr up to 2 liters while crystallization takes place. The resulting precipitate is collected by filtration, washed with water and dried on a steam bath to give 2.55 g of methyl 4 alpha,6,9 alpha-trifluoro-11 beta-hydroxy-16 alpha-methyl-3-oxo-17 alpha-propionyloxyandrosta-1,5-diene 17 beta-thiocarboxylate, m.p. 198°–199.5° C., $[\alpha]_D39°$ (chloroform).

One g of this compound is mixed with 25 ml of methanol in 200 ml of anhydrous potassium carbonate in a suitable reaction vessel under a nitrogen atmosphere at room temperature under stirring for a period of 2 hours, at which time TLC analysis shows the reaction to be complete. One ml acetic acid is added and the methanol is eliminated under reduced pressure to form a small liquid volume which is then diluted with water up to 0.5 liters. The resulting crystalline material is collected by filtration and dried to give 960 mg of a material which is then recrystallized from methylene chloride/methanol. The solvents are eliminated to give 560 mg of methyl 4,6 alpha,9 alpha-trifluoro-11 beta-hydroxy-16 alpha-methyl-3-oxo-17 alpha-propionyloxyandrosta-1,4-diene 17 beta-thiocarboxylate, m.p. 287°–290° C.

Similarly, by following the above procedure set forth in this example but substituting other alkyl, benzyl or phenyl sulfides for methyl sulfide in the first step, other alkyl, benzyl or phenyl compounds of this invention can be prepared.

EXAMPLE 8

By following in principle the procedures set forth in Examples 1, 3 and 5 but substituting the corresponding 16 beta-methyl steroid starting material for the 16 alpha-methyl steroid starting material, the corresponding 16 beta-methyl steroids of this invention are obtained such as 4,6 alpha-trifluoro-11 beta-hydroxy-16 beta-methyl-3-oxo-17 alpha-propionyloxyandrosta-1,4-diene 17 beta-thiocarboxylic acid and the corresponding 17 alpha-alkanoyloxy derivatives along with the alkyl, benzyl and phenyl-17 beta-thiocarboxylates.

EXAMPLE 9

By following in principle the procedures set forth in Examples 1, 3 and 5 but substituting the corresponding 16-unsubstituted steroid starting material for the 16 alpha-methyl steroid starting material, the corresponding 16-unsubstituted steroids of this invention are obtained, such as 4,6 alpha,9 alpha-trifluoro-11 beta-hydroxy-3-oxo-17 alpha-propionyloxyandrosta-1,4-diene 17 beta-thiocarboxylic acid and the corresponding 17 alpha-alkanoyloxy derivatives along with the corresponding alkyl, benzyl and phenyl 17 beta-thiocarboxylates.

EXAMPLE 10

This example sets forth a process for hydrogenating the androsta-1,4-dienes to androst-4-enes of this invention.

A solution of 25 mg of tris-)triphenylphosphine) chlorohodium in

Similarly, 6 ml of benzene and 15 ml of ethanol is stirred under hydrogen for 60 minutes. 4,6 Alpha,9 alpha-trifluoro-11 beta,17 alpha-dihydroxy-16 alphamethyl-3-oxoandrosta-1,4-diene-17 beta-thiocarboxylic acid (250 mg) is added and the resulting solution is stirred under hydrogen at room temperature at atmospheric pressure. After hydrogen uptake is complete, the solution is evaporated to dryness and the residue taken up in a mixture of petroleum ether and methylene chloride. The pure product is isolated by column chromatography on silica gel to give 4,6 alpha,9 alpha-trifluoro-11 beta,17 alpha-dihydroxy-16 alpha-methylandrost-4-ene-17 beta-thiocarboxylic acid. Similarly, by substituting other androsta-1,4-dienes of this invention made according to Examples 1-3 and 5-8 for the compound of formula (I), other corresponding androst-4-enes are prepared.

EXAMPLE 11

This example sets forth a process for preparing an 11-keto compound of this invention by oxidizing any of the 11beta-hydroxy steroids forth in Preparations I–VI.

One g of 4, 6 alpha, 9 alpha-trifluoro-11 beta-hydroxy16 alpha-methyl-3-oxo-17 alpha-propionyloxdyandrost-1,4-diene 17 beta carboxylic acid is dissolved in 50 ml of acetone and treated at room temperature with Jone's reagent (chromic anhydride in dilute sulfuric acid) dropwise until TLC indicates the absence of starting material. The mixture is treated with five drops of isopropyl alcohol to destroy any excess of reagent, then diluted with 50 ml of water and the mixture concentrated under vacuum under reduced pressure to give a crystalline material, namely 4,6 alpha,9alpha-trifluoro-16 alpha-methyl-3,11-dioxy-17 alpha-propionyloxyandrost-1,4-diene 17 beta-carboxylic acid.

The resulting compound is then reacted according to procedures of Examples 1-6 to obtain an 11-keto steroid of this invention.

EXAMPLE 12

A mixture of 0.5 g of methyl 4,6 alpha-difluoro-11 beta-hydroxy-3-oxo-17 alpha-propionyloxyandrost-4-ene 17 beta-thiocarboxylate, 10 ml of dioxane and 0.35 g of 2,3-dichloro-5,6-dicyano-1,4-benzoquinone is refluxed for 10 hours. The mixture is then cooled, filtered and evaporated to dryness. The residue is dissolved in acetone and this solution is then filtered through 10 g of alumina and concentrated to yield methyl 4,6 alpha-difluoro-11 beta-hydroxy-3-oxo-17 alpha-propionyloxyandrosta-1,4-diene 17 beta-thiocarboxylate, which is further purified by recrystallization from acetone:hexane.

Othr androsta-1,4-diene 17 beta-carboxylates of this invention are prepared by the following in principle the above procedure but substituting other appropriate androst-4-ene 17 beta thiocarboxylates for the above-named starting material.

What is claimed is:

1. A compound chosen from those represented by the formula

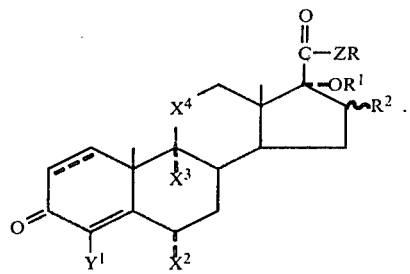

wherein
Z is sulfur
$X^1$ is fluoro, chloro or bromo;
$X^2$ is fluoro, chloro or hydrogen;
$X^3$ is fluoro, chloro, bromo or hydrogen;

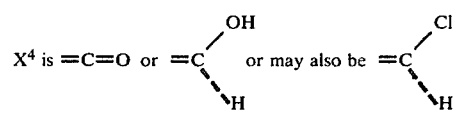

when
$X^3$ is chloro;
R is alkyl of 1 through 6 carbon atoms or phenyl or benzyl optionally substituted with one substituent on the phenyl ring chosen from the group consisting of alkyl of 1 through 4 carbon atoms, alkoxy of 1 through 4 crbon atoms and halo;
$R^1$ is hydrogen or alkanoyl of 2 through 6 carbon atoms when $R^2$ is hydrogen, alpha-methyl or beta methyl, or
$OR^1$ and $R^2$ together are isopropylidenedioxy; and
the solid and broken lines between C-1 and C-2 represent a double or a single bond.

2. A compound of claim 1 wherein R is alkyl of 1–6 carbon atoms, phenyl or benzyl and $R^2$ is alpha-methyl.

3. A compound of claim 1 wherein R is alkyl of 1 or 2 carbon atoms; $X^1$ and $X^2$ are independently fluoro or chloro; $X^3$ is hydrogen fluoro or chloro; and $X^4$ is

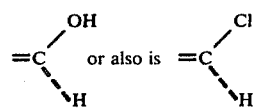

when $X^3$ is chlorine.

4. A compound of claim 3 wherein R is methyl.

5. The compound of claim 4 wherein $X^1$ and $X^2$ are fluoro.

6. The compound of claim 5 wherein $X^1$, $X^2$ and $X^3$ are all fluoro,

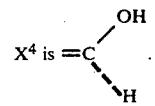

7. The compound of claim 6 wherein R is methyl and $R^1$ is propionyl, namely, methyl 4,6 alpha, 9 alpha-trifluoro-11 beta-hydroxy-16 alpha-methyl-3-oxo-17 alpha-propionyloxyandrosta-1,4 diene 17 beta-thiocarboxylate.

8. The compound of claim 6 wherein R is ethyl and $R^1$ is propionyl, namely, ethyl 4,6 alpha, 9 alpha-trifluoro-11 beta-hydroxy-16 alpha-methyl-3-oxo-17 alpha-propionyloxyandrosta-1,4-diene 17 beta-thiocarboxylate.

9. The compound of claim 2 wherein R is benzyl and $R^1$ is propionyl, namely, benzyl 4,6 alpha, 9 alpha-trifluoro-11 beta-hydroxy-16 alpha-methyl-3-oxo-17 alpha-propionyloxyandrosta-1,4-diene 17 beta-thiocarboxylate.

10. The compound of claim 2 wherein R is phenyl and $R^1$ is propionyl, namely, phenyl 4,6 alpha, 9 alpha-trifluoro-11 beta-hydroxy-16 alpha-methyl-3-oxo-17 alpha-propionyloxyandrosta-1,4diene 17 beta-thiocarboxylate.

11. The compound of claim 5 wherein $X^3$ is chloro and

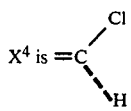

12. The compound of claim 11 wherein R is methyl and $R^1$ is propionyl, namely, methyl 9 alpha, 11 beta-dichloro-4,6 alpha-difluoro-16 alpha-methyl-3-oxo-17 alpha-propionyloxyandrosta-1,4-diene 17d beta-thiocarboxylate.

13. The compound of claim 3 wherein $X^1$ is chloro, $X^2$ and $X^3$ are fluoro and

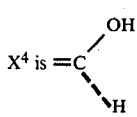

14. The compound of claim 3 wherein $X^2$ is fluoro, $X^1$ and $X^3$ are chloro, and

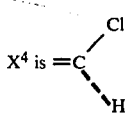

15. A compound of claim 1 wherein R is alkyl of 1 through 6 carbon atoms, phenyl or benzyl; $OR^1$ and $R^2$ together are isopropylidenedioxy;

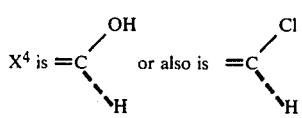

when $X^3$ is chloro; and $X^1$, $X^2$ and $X^3$ are as defined in claim 1.

16. A compound of claim 15 wherein R is alkyl of 1 or 2 carbon atoms; $X^1$ and $X^2$ are independently fluoro or chloro; $X^3$ is hydrogen, fluoro or chloro; and $X^4$ is

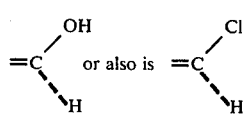

when $X^3$ is chloro.

17. A compound of claim 16 wherein R is methyl.

18. A compound of claim 16 wherein $X^1$ and $X^2$ are both fluoro.

19. A compound of claim 18 wherein R is methyl; $X^1$, $X^2$ and $X^3$ are all fluoro and $X^4$ is

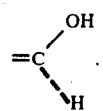

namely methyl 4,6 alpha, 9 alpha-trifluoro-11 beta-hydroxy-16 alpha, 17 alpha-isopropyidenediox-3-oxoandrosta-1,4-diene 17 beta-thiocarboxylate.

20. The compound of claim 18 wherein R is methyl; $X^1$ and $X^2$ are fluoro $X^3$ is chloro; and $X^4$ is

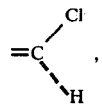

namely methyl 9 alpha, 11 beta-dichloro-4,6 alpha-difluoro-16 alpha, 17 alpha isopropyidenedioxy-3-oxoandrosta-1,4-diene 17 beta-thiocarboxylate.

21. A compound of claim 17 wherein $X^1$ is chloro; $X^2$ and $X^3$ are fluoro;

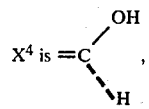

namely, methyl 4-chloro-6 alpha, 9 alpha-difluoro-11 beta-hydroxy-16 alpha, 17 alpha-isopropylidenedioxy-3-oxoandrosta-1,4-diene 17 beta-thiocarboxylate.

22. A compound of claim 17 wherein $X^1$ and $X^3$ are chloro,

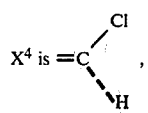

and $X_2$ is fluoro namely 4, 9 alpha, 11 beta-trichloro-6 alpha-fluoro-16 alpha, 17 alpha-isopropylidenedioxy-3-oxoadrosta-1,4-diene 17 beta-thiocarboxylate.

23. A pharmaceutical composition for treating inflammation in a mammal which comprises, as the active ingredient, at least one compound of claim 1 in combination with at least one pharmaceutical excipient.

24. A pharmaceutical composition for treating inflammation in a mammal which comprises, as the active ingredient, at least one compound of claim 2 in combination with at least one pharmaceutical excipient.

25. A pharmaceutical composition for treating inflammation in a mammal which comprises, as the active ingredient, at least one compound of claim 3 in combination with at least one pharmaceutical excipient.

26. A pharmaceutical composition for treating inflammation in a mammal which comprises, as the active ingredient at least one compound of claim 4 in combination with at least one pharmaceutical excipient.

27. A pharmaceutical composition for treating inflammation in a mammal which comprises, as the active ingredient at least one compound of claim 15 in combination with at least one pharmaceutical excipient.

28. A pharmaceutical composition for treating inflammation in a mammal which comprises, as the active ingredient, at least one compound of claim 16 in combination with at least one pharmaceutical excipient.

29. A pharmaceutical composition for treating inflammation in a mammal which comprises, as the active ingredient at least one compound of claim 17 in combination with at least one pharmaceutical excipient.

30. A process for treating inflammation in a mammal which comprises administering a compound of claim 1 to said mammal in an amount sufficient to effect an anti-inflammatory response in said mammel.

31. A process for treating inflammation in a mammal which comprises administering a compound of claim 2 to said mammal in an amount sufficient to effect an anti-inflammatory response in said mammel.

32. A process for treating inflammation in a mammal which comprises administering a compound of claim 3 to said mammal in an amount sufficient to effect an anti-inflammatory response in said mammal.

33. A process for treating inflammation in a mammal which comprises administering a compound of claim 4 to said mammal in an amount sufficient to effect an anti-inflammatory response in said mammel.

34. A process for treating inflammation in a mammal which comprises administering a compound of claim 15 to said mammal in an amount sufficient to effect an anti-inflammatory response in said mammel.

35. A process for treating inflammation in a mammal which comprises administering compound of claim 16 to said mammal in an amount sufficient to effect an anti-inflammatory response in said mammel.

36. A process for treating inflammation in a mammal which comprises administering compound of claim 17 to said mammal in an amount sufficient to effect an anti-inflammatory response in said mammel.

* * * * *